United States Patent [19]

Rakhit et al.

[11] Patent Number: 5,198,425
[45] Date of Patent: Mar. 30, 1993

[54] INHIBITORS OF BACTERIAL RIBONUCLEOTIDE REDUCTASE

[75] Inventors: Sumanas Rakhit, Dollard des Ormeaux; Raymond Plante, Laval; Gregory P. Cosentino, Montreal, all of Canada

[73] Assignee: Bio-Mega, Inc., Laval, Canada

[21] Appl. No.: 900,366

[22] Filed: Jun. 18, 1992

Related U.S. Application Data

[63] Continuation of Ser. No. 573,095, Aug. 27, 1990, abandoned.

[30] Foreign Application Priority Data

Aug. 30, 1989 [CA] Canada .................................. 609873

[51] Int. Cl.$^5$ ..................... A61K 37/00; A61K 37/02; C07K 5/00; C07K 7/00
[52] U.S. Cl. ........................................ 514/14; 514/15; 530/326; 530/327; 530/328
[58] Field of Search ..................... 514/14, 15; 530/326, 530/327, 328

[56] References Cited

U.S. PATENT DOCUMENTS 4,814,432  3/1989  Freidinger et al. .................. 530/329

FOREIGN PATENT DOCUMENTS 8808452  11/1988  PCT Int'l Appl. .

OTHER PUBLICATIONS

B. van't Riet, "Synthesis of Hydroxy-and Amino-Substituted Benzohydroxamic Acids: Inhibition of Ribonucleotide Reductase and Antitumor Activity", J. Med. Chem. 22(5): 589-592 (1979).

Gaudreau et al., "Structure-Activity Studies on Synthetic Peptides Inhibiting Herpes Simplex Virus Ribonucleotide Reductase", J. Biol. Chem. 262(26): 12413-12416 (1987).

Spector et al., "2-Acetylpyridine 5-[(dimethylamino)-thiocarbonyl]-thiocarbonohydrazone (A1110U), a Potent Inactivator of Ribonucleotide Reductases of Herpes Simplex and Varicella-Zoster Viruses and a Potentiator of Acyclovir", Proc., Natl. Acad. Sci. USA 86: 1051-1055 (1989).

*Primary Examiner*—Merrell C. Cashion, Jr
*Assistant Examiner*—A. M. Davenport
*Attorney, Agent, or Firm*—David E. Frankhouser; Daniel Reitenbach; Mary-Ellen M. Timbers

[57] ABSTRACT

Disclosed herein are peptides of the formula $$Y-R^1-R^2-R^3-R^4-R^5-R^6-R^7-R^8-R^9-Z$$

wherein $R^1$ to $R^9$ are designated amino acid residues; Y is hydrogen or lower alkanoyl, or Y is the hexapeptide radical W-Ile-$R^{10}$-Ser-$R^{11}$-Val-$R^{12}$ wherein W is hydrogen or lower alkanoyl and $R^{10}$, $R^{11}$ and $R^{12}$ are designated amino acid residues, or Y is a fragment of the hexapeptide radical wherein from one to five of the amino acid residues (i.e. Ile to Val) may be deleted serially from the amino terminus of the hexapeptide radical; and Z is hydroxy, amino, lower alkylamino or di(lower alkyl)amino. The peptides inhibit bacterial ribonucleotide reductase and are indicated for preventing or ameliorating bacterial infections.

9 Claims, No Drawings

INHIBITORS OF BACTERIAL RIBONUCLEOTIDE REDUCTASE

This is a continuation of application Ser. No. 573,095, filed Aug. 27, 1990 and now abandoned.

FIELD OF THE INVENTION

This invention relates to inhibitors of bacterial ribonucleotide reductase and to a means for preventing or ameliorating bacterial infections. More specifically, this invention relates to peptide derivatives (hereinafter called "peptides") having bacterial ribonucleotide inhibiting properties, to processes for their production, to pharmaceutical compositions of the peptides, and to their use for treating bacterial infections.

BACKGROUND OF THE INVENTION

Ribonucleotide reductase (RNR) is the enzyme responsible for the reductive conversion of ribonucleotides to deoxyribonucleotides. This conversion is the rate determining step in the synthesis of deoxyribonucleic acid (DNA), an essential principle for the growth and replication of eucaryotic cells and procaryotic cells including virions. During the past few years, increasing attention has been given to searching for inhibitors of RNR with the aim of developing new therapeutic agents for controlling cell growth and replication. For example, B. van't Riet et al., J. Med. Chem., 22, 589 (1979) have described a series of benzohydroxamic acids which inhibited mammalian RNR and exhibited antineoplastic activity. P. Gaudreau et al., J. Biol. Chem., 262, 12413 (1987) described a group of peptides which selectively inhibited herpes simplex virus RNR, noting that the peptides were important tools to study the inhibition of herpes viral replication; see also R. Friedinger et al., U.S. Pat. No. 4,814,432, issued Mar. 21, 1989, describing a series of herpes simplex RNR inhibiting peptides. T. Spector et al., Proc. Natl. Acad. Sci. USA 86, 1051 (1989), described a hydrazone derivative as a potent inhibitor of herpes simplex RNR and that a combination of the derivative with acyclovir produced synergistic therapy for the topical treatment of HSV-infected animals. W. J. Dobrogosz and S. E. Lindgren, PCT patent application WO88/08452, published Nov. 3, 1988, have reported the isolation of an antibiotic (reuterin) with RNR inhibiting properties which was active against certain bacteria, yeast and protozoa.

Notwithstanding the attention given the RNR inhibitors, only one such inhibitor has achieved the status as being available to the physician as a therapeutic agent, namely the antineoplastic agent hydroxyurea. Hence, there is a need for RNR inhibitors with improved activity and specificity.

The present application discloses a new group of peptides which specifically inhibit bacterial RNR. This attribute, together with a relative lack of toxicity, renders the peptides useful as antibacterial agents.

SUMMARY OF THE INVENTION

The peptides of this invention are represented by formula 1

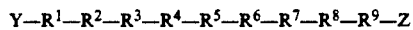

$$Y-R^1-R^2-R^3-R^4-R^5-R^6-R^7-R^8-R^9-Z \quad 1$$

wherein
$R^1$ is Thr, Ser or Val
$R^2$ is Asp or Glu,
$R^3$ is Asp or Glu,
$R^4$ is Leu, Ile or Val,
$R^5$ is Ser or Thr,
$R^6$ is Asn or Gln,
$R^7$ is Phe or (4-halophenyl)methyl,
$R^8$ is Gln or Asn,
$R^9$ is Leu, Ile or Phe,
Y is hydrogen or lower alkanoyl, or
Y is the hexapeptide radical W-Ile-$R^{10}$-Ser-$R^{11}$-Val-$R^{12}$ wherein W is hydrogen or lower alkanoyl, $R^{10}$ is Asp or Glu, $R^{11}$ is Glu or Gln and $R^{12}$ is Asp or Asn, or
Y is a fragment of said hexapeptide radical wherein W, $R^{10}$, $R^{11}$ and $R^{12}$ are as defined hereinabove and wherein from one to five of the amino acid residues (i.e. Ile to Val) may be deleted serially from the amino terminus of the hexapeptide radical; and
Z is hydroxy, amino, lower alkylamino or di(lower alkyl)amino;
or a therapeutically acceptable salt thereof.

A preferred group of the peptides is represented by formula 1 wherein $R^1$ to $R^9$, inclusive, are as defined hereinabove, Y is lower alkanoyl, and Z is hydroxy or amino; or a therapeutically acceptable salt thereof.

Another preferred group of the peptides is represented by formula 1 wherein $R^1$ to $R^9$, inclusive, are as defined hereinabove, Y is the hexapeptide radical or a fragment of the hexapeptide radical, as defined hereinabove, and Z is hydroxy or amino; or a therapeutically acceptable salt thereof.

A more preferred group of the peptides is represented by formula 1 wherein $R^1$ is Thr or Ser, $R^2$, $R^3$, $R^5$, $R^6$ and $R^8$ are as defined hereinabove, $R^4$ is Leu or Ile, $R^7$ is Phe, $R^9$ is Leu or Ile, Y is acetyl, and Z is hydroxy or amino; or a therapeutically acceptable salt thereof.

Another more preferred group of the peptides is represented by formula 1 wherein $R^1$ to $R^9$, inclusive, are as defined in the last instance, Y is the aforementioned hexapeptide radical or a fragment of the hexapeptide radical wherein W is hydrogen or acetyl and $R^{10}$ to $R^{12}$, inclusive, are as defined hereinabove, and Z is hydroxy or amino; or a therapeutically acceptable salt thereof.

A most preferred group of the peptides is represented by formula 1 wherein $R^1$ is Thr, $R^2$ and $R^3$ each independently is Asp or Glu, $R^4$ is Leu, $R^5$ is Ser, $R^6$ is Asn, $R^7$ is Phe, $R^8$ is Gln, $R^9$ is Leu, Y is acetyl, and Z is hydroxy; or a therapeutically acceptable salt thereof.

Another most preferred group of the peptides is represented by formula 1 wherein $R^1$ to $R^9$, inclusive, are defined in the last instance, Y is the aforementioned hexapeptide radical or a fragment of the hexapeptide radical wherein W is hydrogen or acetyl, $R^{10}$ is Asp or Glu, $R^{11}$ is Glu, $R^{12}$ is Asp or Asn, and Z is hydroxy; or a therapeutically acceptable salt thereof.

Included within the scope of this invention is an antibacterial composition comprising an antibacterially effective amount of a peptide of formula 1, or a therapeutically acceptable salt thereof, and a pharmaceutically or veterinarily acceptable carrier.

Also included within the scope of this invention is a method for preventing or ameliorating bacterial infections in a mammal which comprises administering to the mammal an antibacterially effective amount of a peptide of formula 1, or a therapeutically acceptable salt thereof.

Also the invention involves a method of inhibiting the activity of bacterial ribonucleotide reductase which comprises contacting the enzyme with an amount of a peptide of formula 1 which will prevent the enzyme's capacity to catalyze the reduction of ribonucleotide diphosphates to deoxyribonucleotide diphosphates.

Processes for preparing the peptides of formula 1 are described hereinafter.

DETAILS OF THE INVENTION

General

The term 'residue' with reference to an amino acid means a radical derived from the corresponding α-amino acid by eliminating the hydroxyl of the carboxy group and one hydrogen of the α-amino group.

In general, the abbreviations used herein for designating the amino acids and the protective groups are based on recommendations of the IUPAC-IUB Commission of Biochemical Nomenclature, see European Journal of Biochemistry, 138, 9 (1984). For instance, Val, Thr, Glu, Gln Ile, Asp, Phe, Ser, Leu and Asn represent the residues of L-valine, L-threonine, L-glutamic acid, L-glutamine, L-isoleucine, L-aspartic acid, L-phenylalanine, L-serine, L-leucine and L-asparagine, respectively.

The symbol "Ac", when used herein as a prefix to a three letter symbol for an amino acid residue, denotes the N-acetyl derivative of the amino acid; for example, "AcPhe" represents the residue of N-acetyl-L-phenylalanine.

The amino acid residues possess the L-configuration, including those with prefixes such as lower alkanoyl and acetyl. The starting material for providing the amino acid residues, usually the corresponding Nα-protected amino acids are commercially available or can be prepared by conventional methods.

The term "halo" as used herein means a halo radical selected from bromo, chloro, fluoro or iodo.

The term "lower alkanoyl" means an alkanoyl group containing two to six carbon atoms and includes acetyl, 1-oxopropyl, 2-methyl-1-oxopropyl, 1-oxohexyl and the like. Similarly, "lower alkanoic acid" means an alkanoic acid of two to six carbon atoms; for example, acetic acid, propionic acid and 3-methylbutyric acid.

The term "amino" as used herein means an amino radical of formula $-NH_2$. The term "lower alkylamino" as used herein means alkylamino radicals containing one to three carbon atoms and includes methylamino, ethylamino, propylamino and 1-methylethylamino. The term "di(lower alkyl)amino" means an amino radical having two lower alkyl substituents each of which contains one to three carbon atoms and includes dimethylamino, diethylamino, ethylmethylamino and the like.

The term "pharmaceutically acceptable carrier" as used herein means a non-toxic, generally inert vehicle for the active ingredient, which does not adversely affect the ingredient.

The term "veterinarily acceptable carrier" as used herein means a physiologically acceptable vehicle for administering drug substances to domestic animals comprising one or more non-toxic pharmaceutically acceptable excipients which do not react with the drug substance or reduce its effectiveness.

The term "coupling agent" as used herein means an agent capable of effecting the dehydrative coupling of an amino acid or peptide free carboxy group with a free amino group of another amino acid or peptide to form an amide bond between the reactants. The agents promote or facilitate the dehydrative coupling by activating the carboxy group. Descriptions of such coupling agents and activated groups are included in general textbooks of peptide chemistry; for instance, E. Schröder and K. L. Lübke, "The Peptides", Vol. 1, Academic Press, New York, N.Y., 1965, pp 2–128, and K. D. Kopple, "Peptides and Amino Acids", W. A. Benjamin, Inc., New York, N.Y., 1966, pp 33–51. Examples of coupling agents are thionyl chloride, diphenylphosphoryl azide, dicyclohexylcarbodiimide, N-hydroxysuccinimide, or 1-hydroxybenzotriazole in the presence of dicyclohexylcarbodiimide. A very practical and useful coupling agent is (benzotriazol-1yloxy)tris(-dimethylamino)phosphonium hexafluorophosphate, described by B. Castro et al., Tetrahedron Letters, 1219 (1975), see also D.Hudson, J. Org. Chem., 53, 617 (1988), either by itself or in the presence of 1-hydroxybenzotriazole.

PROCESS

The peptides of formula 1 can be prepared by processes which incorporate therein methods commonly used in peptide synthesis such as classical solution coupling of amino acid residues and/or peptide fragments, and if desired, solid phase techniques. Such methods are described, for example, by E. Schröder and K. Lübke, cited above, in the textbook series, "The Peptides: Analysis, Synthesis, Biology", E. Gross et al., Eds., Academic Press, New York, N.Y., 1979-1987, Volumes 1 to 8, and by J. M. Stewart and J. D. Young in "Solid Phase Peptide Synthesis", 2nd ed., Pierce Chem. Co., Rockford, IL, USA, 1984.

A common feature of the aforementioned processes for the peptides is the protection of the labile side chain groups of the various amino acid residues with suitable protective groups which will prevent a chemical reaction from occurring at that site until the protective group is ultimately removed. Usually also common is the protection of an α-amino group on an amino acid or a fragment while that entity reacts at the carboxy group, followed by the selective removal of the α-amino protective group to allow subsequent reaction to take place at that location. Usually another common feature is the initial protection of the C-terminal carboxyl of the amino acid residue or peptide fragment, which is to become the C-terminal function of the peptide, with a suitable protective group which will prevent a chemical reaction from occurring at that site until the protective group is removed after the desired sequence of the peptide has been assembled.

Hence, the peptides of formula 1 can be prepared by a process comprising the stepwise coupling, in the order of the amino acid sequence of the peptide, of the appropriate amino acid residues or peptide fragments (with side chain functional groups duly protected, and with the C-terminal carboxyl of the amino acid residue or peptide fragment, which is to become the C-terminal function of the peptide, duly protected by a C-terminal carboxyl protecting group), in the presence of a coupling agent, to obtain the protected peptide of formula 2

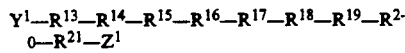

wherein $R^{13}$ is Thr($V^1$), Ser($V^1$) or Val wherein $V^1$ is a protective group for the hydroxyl of Thr or Ser, $R^{14}$ is Asp($V^2$) or Glu($V^2$) wherein $V^2$ is a protective group for the ω-carboxyl of Asp or Glu, $R^{15}$ is Asp($V^2$) or Glu($V^2$) wherein $V^2$ is as defined hereinabove, $R^{16}$ is Leu, Ile or Val, $R^{17}$ is Ser($V^1$) or Thr($V^1$) wherein $V^1$ is as defined hereinabove, $R^{18}$ is Asn or Gln, $R^{19}$ is Phe or (4-halophenyl)methyl, $R^{20}$ is Gln or Asn, $R^{21}$ is Leu, Ile or Phe, $Y^1$ is lower alkanoly or the hexapeptide radical $W^1$-Ile-$R^{22}$-Ser($V^1$)-$R^{23}$-Val-$R^{24}$ wherein $V^1$ is defined hereinabove, $W^1$ is an α-aminoprotective group or lower alkanoyl, $R^{22}$ is Asp($V^2$) or Glu($V^2$) wherein $V^2$ is as defined above, $R^{23}$ is Glu($V^2$) or Gln wherein $V^2$ is as defined above, $R^{24}$ as Asp($V^2$) or Asn wherein $V^2$ is as defined above, or $Y^1$ is a fragment of the last-named hexapeptide radical wherein $W^1$, $R^{22}$, $R^{23}$ are as defined hereinabove and wherein from one to five of the amino acid residues (i.e. Ile to Val) may be deleted serially from the amino terminus of the last-named hexapeptide radical, and $Z^1$ is a classical carboxyl protective group or a resin support; followed by deprotecting (including cleaving the resin support if present), and acylating and/or amidating, if required, the protected peptide of formula 2 to obtain the corresponding peptide of formula 1; and if desired, transforming the peptide of formula 1 into a therapeutically acceptable salt.

The term "resin support", as used herein with reference to $Y^1$, means the radical derived from a solid resin support of the type used in solid phase peptide synthesis. Such resin supports include the well known chloromethylated resins and benzhydrylamine resins, as well as resins which provide a spacer unit between the resin and the first amino acid building block of a peptide-resin system, so that after the peptide portion is assembled the resin can be cleaved selectively from the system.

Examples of resins with spacers incorporated therein are α-(phenylacetamido)benzyl resin (PAB resin), described by E. Giralt et al., Tetrahedron 37, 2007 (1981), and 4-(2-bromo- or 4-(2-chloropropionyl)-phenoxyacetyl BHA resins, photolabile resins described by D. Bellof and M. Mutter, Chemia, 39, 317 (1985).

Examples of side chain protecting groups are benzyl for the protective group ($V^1$) for the hydroxyl of Thr or Ser; and benzyl, 2,6-dichlorobenzyl or preferably cyclohexyl for the protective group ($V^2$) for the ω-carboxyl of Asp or Glu.

Examples of C-terminal carboxyl protecting groups include the classical groups, for example, benzyloxy and 4-nitrophenoxy, and for the present processes include also a "resin support".

In an embodiment of the exclusively solid phase method, the preparation of a peptide of formula 1 in which Z is hydroxy is commenced by coupling the first amino acid relative to the carboxy terminus (the amino acid having an α-amino protective group) with PAB resin in the presence of potassium fluoride or cesium chloride to give the corresponding solid resin support having the first amino acid (with $N^α$-protection) linked thereto. The next step is the removal of the α-amino protective group of the incorporated amino acid to give the free α-amino group. In the instance where the α-amino protective group is a t-butyloxycarbonyl, trifluoroacetic acid in methylene chloride or chloroform, or hydrochloric acid in dioxane, is used to effect the deprotection. The deprotection is carried out at a temperature between about 0° C. and room temperature.

Other standard cleaving reagents and conditions for removal of specific α-amino protective groups may be used as described by E. Schröder and K. Lübke, in "The Peptides", Vol. 1, Academic Press, New York, N.Y., 1965, pp. 72-75. After removal of the α-amino protective group from the last mentioned intermediate, the remaining α-amino protected amino acids (with side chain protection when required) are coupled stepwise in the desired order to obtain the corresponding protected peptide of formula 2 attached to the PAB resin. Each protected amino acid is introduced into the reaction system in one to four fold excess and the coupling is effected with a coupling agent (one to three fold excess) in a medium of methylene chloride, dimethylformamide, or mixtures of dimethylformamide and methylene chloride. In cases where incomplete coupling has occured, the coupling procedure is repeated before removal of the α-amino protective group, prior to the coupling of the next protected amino acid. The success of the coupling reaction at each stage of the synthesis is monitored by the ninhydrin reaction as described by E. Kaiser et al., Anal. Biochem., 34, 595 (1970).

The preceding protected peptide of formula 2 thereafter is simultaneously cleaved from the resin and deprotected by treatment with liquid hydrogen fluoride to give the corresponding peptide of formula 1 in which Z is hydroxy.

When it is desired to prepare the C-terminal primary amide of formula 1 (Z=$NH_2$), the peptide can be prepared by the solid phase method using a benzhydrylamine resin and incorporating into the process the cleavage of the resulting resin-bound peptide and any required deprotection according to known procedures such as described by Stewart and Young, supra.

Alternatively, a convenient and practical method for preparing the preceding C-terminal primary amide, as well as the corresponding secondary and tertiary amides (i.e. peptides of formula 1 wherein Z is lower alkylamino or di(lower alkyl)amino, respectively, involves the solid phase method with a photolabile resin serving as the resin support. For instance, the stepwise coupling of the appropriate amino acid residues to 4-(2-chloropropionyl)phenoxyacetyl BHA resin, noted above, gives the protected peptide of formula 2 in which $Z^1$ is 4-(2-oxypropionyl)phenoxyacetyl BHA-resin. Subsequent photolysis of a suspension or solution of the latter peptide-resin (350 nm, 0° C., 6 to 24 hours) gives the corresponding protected peptide of formula 2 in which $Z^1$ is hydroxy. Coupling of the latter protected peptide with benzylamine or the appropriate lower alkylamine, e.g. methylamine or ethylamine, or the appropriate di(lower alkyl)amine, e.g. dimethylamine or ethylmethylamine, yields the respective protected peptide of formula 2 in which $Z^1$ is benzylamino, lower alkylamino or di(lower alkyl)amino. Deprotection of the latter protected peptide, for example with hydrofluoric acid, provides the corresponding C-terminal primary, secondary or tertiary amide of formula 1.

The terminal amino acylated derivatives of the peptides of formula 1, e.g. peptides of formula 1 wherein Y is lower alkanoyl or Y is the hexapeptide radical or fragment thereof wherein W is lower alkanoyl, are obtained from the corresponding free N-terminal amino peptide (with side chain protection) by treatment with an appropriate acylating agent under suitable conditions; for instance, by treatment with the appropriate acid chloride or acid anhydride in the presence of a strong organic base, e.g. 1-oxobutylchloride with diisopropylethylamine or N-methylmorpholine, or by treatment with a molar equivalent of the appropriate lower alkanoic acid in the presence of a coupling agent; preferably (benzotriazol-1-yloxy)tris(dimethylamino)phosphonium hexafluorophosphate, alone or in combination with 1-hydroxybenzotriazole; followed by conventional deprotection.

The peptide of formula 1 of this invention can be obtained in the form of therapeutically acceptable salts.

In the instance where a particular peptide has a residue which functions as a base, examples of such salts are those with organic acids, e.g. acetic, lactic, succinic, benzoic, salicylic, methanesulfonic or p-toluenesulfonic acid, as well as a polymeric acids such as tannic acid or carboxymethylcellulose, and also salts with inorganic acids such as hydrohalic acids, e.g. hydrochloric acid, or sulfuric acid, or phosphoric acid. If desired, a particular acid addition salt is converted into another acid addition salt, such as a non-toxic, pharmaceutically acceptable salt, by treatment with the appropriate ion exhange resin in the manner described by R. A. Boissonnas et al., Helv. Chim. Acta, 43, 1849 (1960).

In the instance where a particular peptide has one or more free carboxy groups, example of such salts are those with the sodium, potassium or calcium cations, or with strong organic bases, for example, triethylamine of N-methylmorpholine.

In general, the therapeutically acceptable salts of the peptides of formula 1 are biologically fully equivalent to the peptides themselves.

BIOLOGICAL ASPECTS

The RNR inhibiting and antibacterial properties of the peptides of formula 1, or a therapeutically acceptable salt thereof, can be demonstrated by biochemical and biological procedures.

As exemplified hereinafter, the RNR inhibitory effect of the peptides of formula 1 on bacterial RNR can be demonstrated in the "Inhibition of Bacterial Ribonucleotide Reductase Assay", the procedure of which is based on similar assays reported by E. A. Cohen et al., J. Gen. Virol., 66, 733 (1985) and by H. L. Elford et al., Adv. Enz. Reg., 19, 151 (1981).

Noteworthy, is the finding that when the latter assay is repeated with mammalian RNR's, including human RNR, a selective inhibition of bacterial RNR is shown.

The ability of the peptides of formula 1 to selectively inhibit bacterial RNR renders the peptides useful as agents for treating pathogenic infections.

In the laboratory, the antibacterial effect of the peptides can be demonstrated in tests with pathogenic bacteria in culture. Minimum inhibitory concentration is used as the evaluation parameter. The methods are described in various publications; for example, F. Kavanagh in "Industrial Microbiology", B. M. Miller and W. Litsky (eds.), McGraw-Hill, New York, N.Y., 1976, pp 13–46.

When the peptides of this invention, or their therapeutically acceptable salts, are employed as agents for combatting disease states associated with bacterial infection, they are administered topically or systemically to warm-blooded animals, e.g. humans, dogs, horses, in combination with pharmaceutical acceptable carriers, the proportion of which is determined by the solubility and chemical nature of the peptide, chosen route of administration and standard biological practice. For topical application, the peptides may be formulated in the form of solutions, creams, or lotions in pharmaceutically acceptable vehicles containing 1.0 to 10 percent, preferably 2 to 5 percent of the agent, and may be administered topically to the infected area of the body.

For systemic administration, the peptides of formula 1 are administered by either intravenous, subcutaneous or intramuscular injection, in compositions with pharmaceutically acceptable vehicles or carriers. For administration by injection, it is preferred to use the peptides in solution in a sterile aqueous vehicle which may also contain other solutes such as buffer or preservatives as well as sufficient quantities of pharmaceutically acceptable salts or of glucose to make the solution isotonic.

Examples of suitable excipients or carriers are found in standard pharmaceutical texts, e.g. in "Remington's Pharmaceutical Sciences", 16th ed, Mack Publishing Company, Easton, Penn., USA, 1980.

The dosage of the peptides will vary with the form of administration and the particular compound chosen. Furthermore, it will vary with the particular host under treatment. Generally, treatment is initiated with small dosages substantially less than optimum dose of the compound. Thereafter, the dosage is increased by small increments until the optimum effect under the circumstances is reached. In general, the peptides of this invention are most desirably administered at a concentration level that will generally afford effective results, i.e. antibacterial effects, without causing any harmful or deleterious side effects.

When used systemically as an antibacterial agent, the peptide of formula 1 is administered at a dose of 100 mcg to 1000 mcg per kilogram of body weight per day, although the aforementioned variations will occur. However, a dosage level that is in the range of from about 100 mcg to 500 mcg per kilogram of body weight per day is most desirably employed in order to achieve effective results.

In addition, as an antibacterial agent, the peptides of formula 1 can be used for cleaning and disinfecting laboratory equipment, surgical instruments, locker rooms, or shower rooms of sensitive bacteria organisms. For such purposes it is preferred to use 0.1–10% solutions of the peptide in a lower alkanol, preferably methanol, and to dilute the solution with 10–100 volumes of water containing 0.001–0.1% of a non-ionic surface-active agent, for example, polysorbate 80 U.S.P., immediately before applying the preparation to the objects to be cleaned and disinfected.

Without further elaboration, it is believed that one skilled in the art can, using the preceding description, utilize the invention to its fullest extent, the invention encompassing a peptide, or a functional derivative thereof, for use as a antibacterial agent, capable of inhibiting the activity of bacterial RNR, the peptide having an amino acid sequence of Thr-Asp-Asp-Leu-Ser-Asn-Phe-Gln-Leu. The following specific embodiments are, therefore, to be construed as not limitative of the remainder of the disclosure.

The following examples illustrate further this invention. Solution percentages or ratios express volume to volume relationship, unless stated otherwise. Abbreviations used in the examples include Boc: t-butyloxycarbonyl; BOP: (benzotriazol-1-yloxy)tris(dimethylamino)-phosphonium hexafluorophosphate; Bzl: benzyl; $CH_2Cl_2$: methylene chloride; Chx1: cyclohexyl; 2,6-DiClBzl: 2,6-dichlorobenzyl; DCC: $N,N^1$-dicyclohexylcarbodiimide; DMF: dimethylformamide; $Et_2O$: diethyl ether; EtOH: ethanol; HF: hydrofluoric acid; HOBT: 1-hydroxybenzotriazole; MeOH: methanol; TFA: trifluoroacetic acid.

EXAMPLE 1

Preparation of Boc-Leu-CH$_2$-PAB Resin

Boc-Leu-OH (12.9 g, 56 mmol) and potassium fluoride (7.31 g, 126 mmol) were added to a mechanically stirred suspension of α-(4-chloromethylphenylacetamido)benzyl-copoly(styrene-1% divinylbenzene) resin (25 g, 14 mmol, described by Giralt et al., supra) in DMF (1 l). The mixture was stirred at 70° C. for 24 h, and then allowed to cool to ambient temperature. The solid was collected by filtration, washed successively with 100 ml portions of DMF, DMF-H$_2$O (1:1), H$_2$O-dioxane (1:1), dioxane, MeOH, CH$_2$Cl$_2$ and EtOH, and dried under reduced pressure to give 25.3 g of the title compound. The leucine content of the product was 0.40 mmol/g as determined by deprotection of an aliquot and picric acid titration according to the method of B. F. Gisin, Anal. Chim. Acta, 58, 248 (1972).

EXAMPLE 2

Preparation of the N-acetyl Nonapeptide of the Formula:

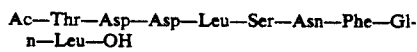

The title compound was synthesized by a modification of the solid-phase method of R. B. Merrifield, J. Amer. Chem. Soc., 85, 2149 (1963). Applying the method, the corresponding protected nonapeptide-resin having the correct sequence of amino acid residues was assembled by stepwise addition of the amino acids residues to Boc-Leu-CH$_2$PAB resin, i.e. the title compound of Example 1. The following protocol was used: (a) Boc-deprotection: 30% TFA in CH$_2$Cl$_2$ (2 times, firstly for 5 min then for 25 min); (b) wash: CH$_2$Cl$_2$ (3 times for 2 min each); (c) wash: isopropanol (2 min); (d) neutralization: 5% diisopropylethylamine in CH$_2$Cl$_2$ (2 times for 2 min each); (e) amino acid coupling: achieved by the method of D. Hudson, J. Org. Chem., 53, 617 (1988) using the appropriate protected amino acid (2.1 molar equivalents per mmol of the Boc-Leu-CH$_2$-PAB resin) and BOP-HOBT (2.2 and 1.1 molar equivalents, respectively, per mmol of the Boc-Leu-CH$_2$-PAB resin) in the presence of N-methylmorpholine (6–8 molar equivalents providing pH 8 for the reaction mixture) in CH$_2$Cl$_2$ or DMF; the reaction time for coupling varied from 3 to 5 h; and (f) wash: CH$_2$Cl$_2$ or DMF (2 times for 2 min each). The Gln and Asn residues were coupled in DMF after activation of the corresponding Boc-amino acid with DCC-HOBT and removal by filtration of the N,N$^1$-dicyclohexylurea formed during the activation process.

The Boc group gave N$^\alpha$ protection for all amino acids. Side chain protection was as follows: Bzl for Thr and Ser, and Chxl for Asp. After each coupling, the completeness of the reaction was checked by the ninhydrin test, E. Kaiser et al., Anal. Biochem., 34, 595 (1970). The N-terminal acetylation was accomplished by coupling the free N-terminal amino protected peptide-resin with a molar equivalent of acetic acid using the BOP-HOBT method, or with acetic anhydride in the presence of diisopropylethylamine in CH$_2$Cl$_2$ or DMF.

On completion of the peptide sequence, the protected nonapeptide-resin was collected on a filter, washed with CH$_2$Cl$_2$ and EtOH and dried under reduced pressure over phosphorous pentoxide for 24 h to give the corresponding protected nonapeptide-resin (i.e. peptide-resin). The nonapeptide was cleaved from the peptide-resin by using HF (5 ml per g of peptide-resin) in the presence of distilled anisole (1 ml per g of peptide-resin) and ethanedithiol (0.2 ml per g of peptide-resin). The mixture was maintained at −20° C. for 40 min and then at 0°–5° C. for 40 min, with vigorous stirring. After evaporation of HF, the residue was triturated with Et$_2$O. The mixture was filtered through diatomaceous earth. After washing with Et$_2$O, the filter cake was dried under reduced pressure. The residual solid was washed with several portions of 10% aqueous acetic acid, and then with 0.1M aqueous NH$_4$OH (total volume: 40 ml per g of the peptide-resin). All the aqueous filtrates were mixed at 0° C. (pH 6) and lyophilized to afford a white solid residue.

Purification of the solid residue to greater than 95% homogeneity was accomplished by reversed phase HPLC with a Waters model 600 multisolvent delivery system (Waters, Milford, MA, USA) equipped with a UV detector and using a Whatman Partisil ® 100DS-3 C-18 column (2.2×50 cm$^2$), 10 micron particle size. The elution was done with a gradient of acetonitrile in 0.1% aqueous TFA such as:

a) initial 10% acetonitrile in 0.1% aqueous TFA for 20 min, b) followed by gradually increasing the concentration of acetonitrile to 20% over a period of 20 min, followed by gradually increasing the concentration to 40% acetonitrile over a period of 50 min.

Pure fractions, as determined by analytical HPLC, were pooled and lyophilized to afford the title nonapeptide as trifluoroacetate. Analytical HPLC showed the product to be at least 95% homogeneous. Amino acid analysis: Asp+Asn, 3.08; Thr, 0.92; Ser, 0.92; Gln, 1.01; Leu, 2.03; Phe, 1.04; FAB-MS, calcd: 1093.49, found: 1094 (M+H), etc.

EXAMPLE 3

Inhibition of E. coli Ribonucleotide Reductase Assay

1) Preparation of Extracts Containing Active RNR (a) Bacterial strain

E. coli B3 obtained from Dr. B. -M. Sjöberg, University of Stockholm, Stockholm, Sweden.

(b) Fermentation

Cells were produced in 80 l batches using a standard New Brunswick Scientific Co. pilot-scale fermenter. A two-stage fermentation process was utilized whereby an inoculum of cells was first grown in thymine-rich Davis Medium (3.5 l) for 16 h at 37° C. to an optical density of 0.117 (λ=640 nm). A 3.2 l portion from the first stage was passed to 80 l of thymine-poor Davis Medium in the fermenter and incubated a further 28 h at 37° C. (200 rpm agitation and 1 vvm aeration). Final optical density of cells in the production bioreactor was 0.82 at a fivefold dilution (λ=640 nm).

|  | Thymine Rich Davis Medium | Thymine Poor Davis Medium |
|---|---|---|
| Sodium Citrate | 0.5 g/l | 0.25 g/l |
| Potassium Phosphate Monobasic | 3.0 g/l | 1.5 g/l |
| Potassium Phosphate Dibasic | 7.0 g/l | 3.5 g/l |
| MgSO$_4$ | 0.1 g/l | 0.05 g/l |
| (NH$_4$)$_2$SO$_4$ | 1 g/l | 0.5 g/l |
| Ethylenediaminetetracetic Acid | 50 μM | 25 μM |
| CaCl$_2$ | 5 μM | 2.5 μM |
| FeCl$_3$ | 60 μM | 30 μM |

-continued

| | Thymine Rich Davis Medium | Thymine Poor Davis Medium |
|---|---|---|
| $ZnSO_4$ | 0.6 μM | 0.3 μM |
| $CuSO_4$ | 60 μM | 30 μM |
| $MnSO_4$ | 0.6 μM | 0.3 μM |
| $CoCl_2$ | 0.75 μM | 0.375 μM |
| glucose | 0.2% | 0.2% |
| thymine | 2.0 mg/l | 0.15 mg/l |
| DF287 antifoam (Mazer, Porritts Drive, Illinois, USA) | — | 0.1% |

(c) Preparation of cell extract containing *E. coli* ribonucleotide reductase *E. coli* RR The harvested fermentation media obtained above was subjected to microfiltration followed by high speed centrifugation. The resulting cell pellet was processed according to the following steps. (All steps were performed at 4° C. unless noted otherwise.)

STEP i) Storage: Cells frozen at −80° C. until extraction
ii) Extraction Buffer: 50 mM tris(hydroxymethyl)aminoethane hydrochloride (Tris.-HCl, pH 7.6), 10 mM DL-dithiothreitol (DTT), 0.1% (w/v) Brij 58 ® (polyoxyethylene (20) cetyl ether, Atlas Chemical Industries Inc., Wilmington, Del., U.S.A.), 0.1M NaCl and 10% (w/v) sucrose
iii) Cell Disruption: Cells in extraction buffer are subjected to high speed homogenization in an industrial blender in the presence of alumina abrasive (2 g of alumina abrasive per gram, wet weight, of cells)
iv) Centrifugation: 40,000 times gravity for 60 min; recover supernatant
v) Precipitation #1: A solution of 5% (w/v) streptomycin sulfate in 50 mM Tris.-HCl (pH 7.6) and 1 mM DTT added dropwise to supernatant to give a final concentration in the mixture of 1% (w/v) of streptomycin sulfate.
vi) Centrifugation: 40,000 times gravity for 60 min; recover supernatant
vii) Precipitation: Saturated $(NH_4)_2SO_4$ in Tris.HCl/DTT buffer (see step v) added slowly to supernatant to yield 60% saturated solution; solution agitated for 60 min
viii) Centrifugation: 17,000 times gravity for 60 min; recover pellet
ix) Solubilization: Take up pellet in minimum volume of 50 mM Tris.HCl (pH7.6), 10 mM DTT
x) Dialysis: Dialysis carried out overnight (18 h) using standard dialysis tubing (nominal molecular weight cut-off limit of 12,000 to 14,000 daltons) against a 50 fold excess of the solubilization buffer [50 mM Tris.HCl (pH 7.6), 10 mM DTT]
xi) Storage: Frozen at −80° C.

2) Assay Protocol (a) Standard Reaction Mixture

| Component | Amount* |
|---|---|
| HEPES Buffer (pH 7.8) | 50 mM |
| Adenosine Triphosphate | 4 mM |
| DTT | 30 mM |
| $MgCl_2$ | 11.5 mM |
| NaF | 4 mM |
| Cytidine Diphosphate (CDP) | 0.054 mM |
| ($^3$H)CDP (DuPont Chem. Co. Lachine, QC, Canada) | 4.2 μCi/ml |
| Bacitracin | 1 mM |

-continued

| Component | Amount* |
|---|---|
| Test Compound | 1–500 μM |

*Final concentration of component in standard reaction mixture.

(b) Assay Procedure

The activity of RNR was quantitated by following the conversion of radiolabeled cytidine diphosphate to radiolabeled deoxycytidine diphosphate, i.e. ($^3$H)CDP to ($^3$H)dCDP. The amount of cell extract utilized in the assay was that which gave a linear response between enzyme concentration and CDP conversion (ca. 100 μg of protein per assay).

After addition of the cell extract, the assay mixture was incubated at 25° C. for 30 min. The reaction was stopped by immersing the vessel containing the assay mixture in boiling water for 4 min. Nucleotides in the supernatant were then converted to nucleosides by the addition of one part of a *Crotalus adamenteus* snake venom preparation [40 mg/ml of the venon in an aqueous solution of 14 mM tris(hydroxymethyl)aminomethane (pH 8.8) and 46.5 mM $MgCl_2$], to three parts supernatant, followed by incubating the resulting mixture for 60 min at 37° C. The enzymatic reaction was stopped by immersing the vessel containing the reaction mixture in boiling water for 6 min. Thereafter, the mixture is centrifuged at 10,000 rpm on a clinical centrifuge for 5 min.

A 10 μl aliquot of unlabelled nucleoside standards containing 5 mM each of cytidine (C) and deoxycytidine (dC) was added to the supernatant and the resulting mixture was separated by thin layer chromotography on polyethyleneimine-cellulose plates pretreated with boric acid. Elution of 5 μl samples was accomplished using a solution of ethanol/20 mM aqueous ammonium formate (1:1), pH 4.7. Quantitation of radiolabel migrating as C and dC was carried out by visualizing the standards under ultraviolet light and cutting out those sections of the TLC plates for each of the assay lanes. The residues from the sections then were extracted into a buffer of one ml of 20 mM Tris.HCl (pH 7.5)/0.7M $MgCl_2$ by agitating the sections in the buffer for a period of 20 min. Aliquots of scintillation fluid (10 ml) were added to each extract and radiolabel was subsequently quantitated with a LKB-Wallac Beta liquid scintillation counter (LKB-Produkten AB, Bromma, Sweden.) Substrate conversion was calculated as:

$$\frac{(^3H)\text{deoxycytidine}}{(^3H)\text{deoxycytidine} + (^3H)\text{cytidine}}$$

A unit of ribonucleotide reductase activity is defined as that amount which reduces one nmole of CDP/minute under the conditions described above. Activity was calculated from substrate conversion using the following relationship:

$$\left(\begin{array}{c}\text{substrate}\\\text{conversion}\\\text{(sample)}\end{array}\right) - \left(\begin{array}{c}\text{substrate}\\\text{conversion}\\\text{(blank)}\end{array}\right) \times$$

conversion factor = activity units

The conversion factor for the *E. coli* assay was 0.108. Specific activity was expressed as units/mg of protein in the incubation mixture. In one embodiment, the specific activity of the *E.coli* extract was found to be 0.2 units/mg.

The peptides of formula 1 were tested at a minimum of three concentrations. $IC_{50}$'s were estimated from graphs plotting the results for each peptide, the $IC_{50}$ being the concentration of the peptide in micromoles (M) producing 50% of the maximal inhibition of the enzyme.

When the N-acetyl-nonapeptide of Example 2 having the formula Ac-Thr-Asp-Asp-Leu-Ser-Asn-Phe-Gln-Leu-OH was tested according to the assay of this example, an $IC_{50}$ of 400 μM was determined for the compound.

Other examples of peptides within the scope of this invention include:

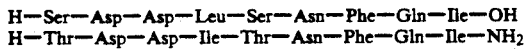
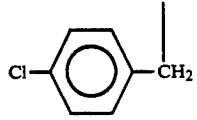
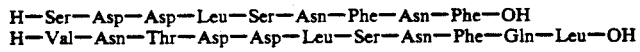

We claim:

1. A peptide consisting essentially of formula 1

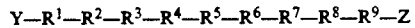

wherein
$R^1$ is Thr, Ser or Val,
$R^2$ is Asp or Glu,
$R^3$ is Asp or Glu,
$R^4$ is Leu, Ile or Val,
$R^5$ is Ser or Thr,
$R^6$ is Asn or Gln,
$R^7$ is Phe or (4-halophenyl)methyl,
$R^8$ is Gln or Asn,
$R^9$ is Leu, Ile or Phe,
Y is hydrogen or lower alkanoyl, or
Y is the hexapeptide radical W-Ile-$R^{10}$-Ser-$R^{11}$-Val-$R^{12}$ wherein W is hydrogen or lower alkanoyl, $R^{10}$ is Asp or Glu, $R^{11}$ is Glu or Gln and $R^{12}$ is Asp or Asn, or
Y is a fragment of said hexapeptide radical wherein W, $R^{10}$, $R^{11}$ and $R^{12}$ are as defined hereinabove and wherein from one to five of the amino acid residues may be deleted serially from the amino terminus of the hexapeptide radical; and
Z is hydroxy, amino, lower alkylamino or di(lower alkyl)amino; or a therapeutically acceptable salt thereof.

2. A peptide as recited in claim 1 wherein Y is lower alkanoyl and Z is hydroxy or amino, or a therapeutically acceptable salt thereof.

3. A peptide as recited in claim 1 wherein Y is the hexapeptide radical or a fragment of the hexapeptide radical and Z is hydroxy or amino, or a therapeutically acceptable salt thereof.

4. A peptide as recited in claim 2 wherein $R^1$ is Thr or Ser, $R^4$ is Leu or Ile, $R^7$ is Phe, $R^9$ is Leu or Ile, Y is acetyl, and Z is hydroxy or amino; or a therapeutically acceptable salt thereof.

5. A peptide as recited in claim 3 wherein Y is the hexapeptide radical or a fragment of the hexapeptide radical wherein W is hydrogen or acetyl and Z is hydroxy or amino; or a therapeutically acceptable salt thereof.

6. A peptide as recited in claim 4 wherein $R^1$ is Thr, $R^2$ and $R^3$ each idependently is Asp or Glu, $R^4$ is Leu, $R^5$ is Ser, $R^6$ is Asn, $R^7$ is Phe, $R^8$ is Gln, $R^9$ is Leu, Y is acetyl, and Z is hydroxy; or a therapeutically acceptable salt thereof.

7. A peptide as recited in claim 5 wherein Y is the hexapeptide radical or a fragment of the hexapeptide radical wherein W is hydrogen or acetyl, $R^{10}$ is Asp or Glu, $R^{11}$ is Glu, $R^{12}$ is Asp or Asn, and Z is hydroxy; or a therapeutically acceptable salt thereof.

8. A peptide as recited in claim 1 having the formula Ac-Thr-Asp-Asp-Leu-Ser-Asn-Phe-Gln-Leu-OH, or a therapeutically acceptable salt thereof.

9. A pharmaceutical composition comprising an antibacterially effective amount of a peptide of formula 1, or a therapeutically acceptable salt thereof, and a pharmaceutically or veterinarily acceptable carrier.

* * * * *